United States Patent [19]

Hall et al.

[11] Patent Number: 4,522,950
[45] Date of Patent: Jun. 11, 1985

[54] 2,3-DIHYDROFURANS USEFUL AS FUNGICIDES

[75] Inventors: Allen L. Hall, Amelia; Richard G. Fayter, Jr., Fairfield, both of Ohio

[73] Assignee: National Distillers and Chemical Corporation, New York, N.Y.

[21] Appl. No.: 503,975

[22] Filed: Jun. 13, 1983

[51] Int. Cl.³ .................. A01N 43/08; C07D 307/30; C07D 307/32
[52] U.S. Cl. ..................... 514/471; 260/464; 514/473; 549/474; 549/479; 549/487; 564/80; 564/190; 568/31
[58] Field of Search ...................... 549/474, 479, 487; 424/285

[56] References Cited

PUBLICATIONS

Pacini et al., J. Org. Chem., 31 (12) 1966, pp. 4133–4137.

*Primary Examiner*—Richard L. Raymond
*Attorney, Agent, or Firm*—Kenneth D. Tremain; Gerald A. Baracka

[57] ABSTRACT

2,4,5-Trisubstituted-2,3-dihydrofurans useful for fungicidal applications are provided herein. The 2,3-dihydrofuran compounds correspond to the general formula

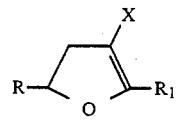

where R is an ethyl or vinyl group, $R_1$ is a $C_{1-10}$ hydrocarbon radical and X is a nitrile, amide or sulfonyl group. The compounds of this invention are effective fungicides for the treatment of seeds and also find use in other agricultural fungicidal applications.

4 Claims, No Drawings

2,3-DIHYDROFURANS USEFUL AS FUNGICIDES

BACKGROUND OF THE INVENTION

1. Field of the Invention

This invention relates to novel 2,3-dihydrofuran derivatives and, more specifically, to certain 2,4,5-trisubstituted 2,3-dihydrofurans which are useful for fungicidal applications.

2. Description of the Invention

Dihydrofurans having a nitrile or amide substituted on the ring are known. For example, a dihydrofuran of the structure

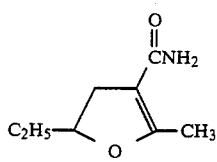

has been reported by Pacini et al. in J. Org. Chem., Vol. 31, p. 4134 (1966). The 2-methyl-5-ethyl-4,5-dihydro-3-furamide is obtained by treating 3-acetyl-4-ethyl-2-oxotetrahydrofuran with aqueous ammonia. 2-Amino-3-cyanofuran of the general structure

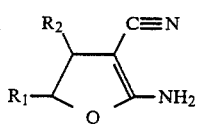

are reported by Yamazaki et al. in Japanese Pat. No. 75 30,080.

SUMMARY OF THE INVENTION

It is an object of this invention to provide novel 2,3-dihydrofuran derivatives which are substituted on the 2,4 and 5 ring positions. It is another object to provide 2,3-dihydrofuran derivatives wherein one of the substituents is a nitrile, amide or sulfonyl group. Still another object of the invention is to provide novel 2,3-dihydrofurans which are useful as fungicides and which can be readily and economically prepared.

These and other objects are accomplished by providing herein a novel class of 2,4,5-trisubstituted-2,3-dihydrofurans corresponding to the general formula

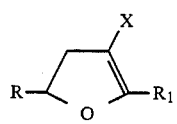

wherein R is an ethyl or vinyl group, $R_1$ is a $C_{1-10}$ hydrocarbon radical which can be aliphatic, cycloaliphatic or aromatic, and X is a nitrile, amide or sulfonyl group. Amide groups correspond to the formula

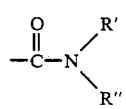

where R' is a $C_{1-10}$ alkyl group, phenyl, benzyl or $C_{1-4}$ alkyl- or alkoxyl-substituted phenyl or benzyl and R" is hydrogen or a radical as defined for R'. Sulfonyl groups correspond to the formula

where R''' is a $C_{1-10}$ alkyl group, phenyl, benzyl, $C_{1-4}$ alkyl- or alkoxyl-substituted phenyl or benzyl or the group

where R' and R" are the same as defined above.

DETAILED DESCRIPTION OF THE INVENTION

The novel 2,4,5-trisubstituted 2,3-dihydrofurans of this invention useful as fungicides have the general formula

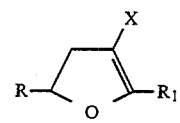

wherein R is an ethyl or vinyl group, $R_1$ is a $C_{1-10}$ hydrocarbon radical and X is nitrile, an amide or sulfonyl group. $R_1$ can be an aliphatic, cycloaliphatic or aromatic hydrocarbon radical. Preferably, $R_1$ is a $C_{1-4}$ alkyl group such as methyl, ethyl, n-propyl, iso-propyl, n-butyl, tert-butyl and sec-butyl. When X is an amide group it will correspond to the formula

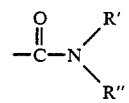

where R' is a $C_{1-10}$ alkyl group, phenyl, benzyl, or $C_{1-4}$ alkyl- or alkoxyl-substituted phenyl or benzyl and R" is hydrogen or a radical as defined for R'. In a preferred embodiment of this invention R' is a $C_{1-4}$ alkyl or phenyl. When X is a sulfonyl group it will correspond to the formula

where R''' is a $C_{1-10}$ alkyl group, phenyl, benzyl, $C_{1-4}$ alkyl- or alkoxyl-substituted phenyl or benzyl, or an amide group of the formula

where R' and R" are the same as defined above.

Illustrative 2,3-dihydrofurans of the above types include:

4-cyano-5-methyl-2-vinyl-2,3-dihydrofuran;
4-cyano-5-methyl-2-ethyl-2,3-dihydrofuran;
4-cyano-5-ethyl-2-vinyl-2,3-dihydrofuran;
4-cyano-5-ethyl-2-ethyl-2,3-dihydrofuran;
4-cyano-5-phenyl-2-vinyl-2,3-dihydrofuran;
4-diethylcarbamyl-5-methyl-2-vinyl-2,3-dihydrofuran;
4-diethylcarbamyl-5-methyl-2-ethyl-2,3-dihydrofuran;
4-diethylcarbamyl-5-ethyl-2-vinyl-2,3-dihydrofuran;
4-phenylcarbamyl-5-methyl-2-vinyl-2,3-dihydrofuran;
4-phenylcarbamyl-5-methyl-2-ethyl-2,3-dihydrofuran;
4-phenylsulfonyl-5-methyl-2-vinyl-2,3-dihydrofuran;
4-phenylsulfonyl-5-methyl-2-ethyl-2,3-dihydrofuran;
4-benzylsulfonyl-5-methyl-2-vinyl-2,3-dihydrofuran;
4-benzylsulfonyl-5-methyl-2-ethyl-2,3-dihydrofuran;
4-(p-methoxyphenylsulfonyl)-5-methyl-2-vinyl-2,3-dihydrofuran;
4-(p-methylphenylsulfonyl)-5-methyl-2-vinyl-2,3-dihydrofuran;
4-(p-methylbenzylsulfonyl)-5-methyl-2-ethyl-2,3-dihydrofuran;
4-phenylsulfonamido-5-methyl-2-vinyl-2,3-dihydrofuran;
4-phenylsulfonamido-5-methyl-2-ethyl-2,3-dihydrofuran; and the like.

The 2,3-dihydrofuran compounds are readily obtained by isomerization of the corresponding cyclopropyl ketone derivative in accordance with the following equation:

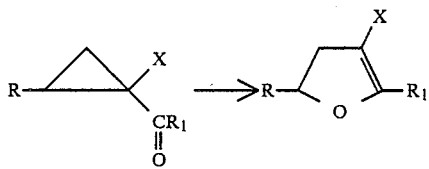

wherein R, $R_1$ and X are the same as previously defined. The isomerization process is fully described in the copending application of R. G. Fayter, Jr. and A. L. Hall entitled PROCESS FOR THE ISOMERIZATION OF CYCLOPROPYL KETONES TO 2,3-DIHYDROFURANS and filed on the same date as the present application as Ser. No. 503,952, now U.S. Pat. No. 4,487,946—details of which are incorporated herein by reference thereto.

The isomerization is typically carried out at a temperature from 60° C. to 200° C. utilizing from about 0.5 to 20 weight percent, based on the cyclopropyl ketone, of an onium catalyst. Most generally, the onium catalyst is present in an amount from 2 to 15 weight percent and is a quaternary ammonium or phosphonium compound containing at least six carbon atoms and corresponding to the formula

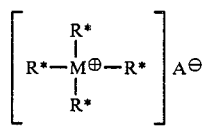

where M is nitrogen or phosphorous, R* represents a hydrocarbon radical having from 1 to 22 carbon atoms, and A is chloride or bromide. Particularly useful onium catalysts for the isomerization process contain at least 10 carbon atoms and include tetrabutylammonium chloride; tetrabutylammonium bromide; dimethyldibenzylammonium chloride; dimethyldibenzylammonium bromide; trimethylbenzylammonium chloride; trimethylbenzylammonium bromide; tricaprylylmethylammonium chloride; tricaprylylmethylammonium bromide; tributylhexadecylphosphonium chloride; tributylhexadecylphosphonium bromide; and the like.

Preferably, the isomerization reaction is carried out in the absence of a diluent or solvent and the cyclopropyl ketone is essentially free of water and caustic. If a solvent or diluent is employed, it must be inert to the reaction conditions and should be easily separable from the 2,3-dihydrofuran at the conclusion of the reaction by distillation or the like. It is also preferred to remove the onium catalyst from the 2,3-dihydrofuran by simple techniques.

The 2,3-dihydrofurans of the present invention are useful as fungicides and are particularly advantageous for use in agricultural fungicidal applications. While they are primarily used for the treatment of seeds, they may also be applied to the plant foliage, to harvested plant parts or to the soil for control of fungal diseases. They may be applied as dusts or in water suspension and can be used in combination with solvents, emulsifiers, dispersants, wetting agents, sticking agents, extenders, and other fungicides. The compounds of this invention are particularly advantageous for the treatment of seeds, such as corn, wheat, barley, oats and soyabeans and exhibit fungistatic activity against plant pathogens.

The following examples illustrate the invention more fully. In these examples, all parts and percentages are on a weight basis unless otherwise indicated.

EXAMPLE I

In accordance with the phase-transfer process of U.S. Pat. No. 4,252,739, N,N-diethyl-1-acetyl-2-vinylcyclopropanecarboxamide was prepared by reacting 114.4 grams acetoacetamide, 110 grams 1,4-dichlorobutene-2, and 40 grams powdered sodium hydroxide. The reaction was carried out in methylene chloride using 16.15 grams tricaprylylmethylammonium chloride as the phase-transfer catalyst for 19 hours at 25° C. At the conclusion of the reaction, the reaction mixture was filtered to remove insoluble-salts and the organic layer dried and stripped under vacuum to remove the methylene chloride. The resulting crude oil (78 grams) consisting primarily of N,N-diethyl-1-acetyl-2-vinylcyclopropanecarboxamide was distilled and chromatographically separated to obtain essentially pure N,N-diethyl-1-acetyl-2-vinylcyclopropanecarboxamide.

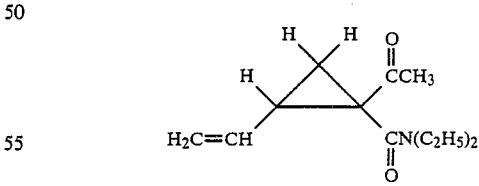

Boiling point 92°–95° C. at 0.01 mm Hg
Mass spectrum m/e 209(M+)
nmr (CDCl$_3$)τ4.50–5.05(3 vinyl H, mult.);

$$6.59(4H-CO\overset{|}{N}-CH_2-), q);$$

7.10–7.65(1H(2-ring position), mult.); 7.85(3H methyl-(—COCH$_3$), s); 8.1–8.70(2H(3-ring position), mult.(partially hidden));

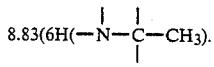
8.83(6H(—N—C—CH$_3$).

The N,N-diethyl-1-acetyl-2-vinylcyclopropanecarboxamide was combined with 15 mole percent tricaprylylmethylammonium chloride and essentially completely isomerized to 4-diethylcarbamyl-5-methyl-2-vinyl-2,3-dihydrofuran by heating for 5 hours at 125° C.

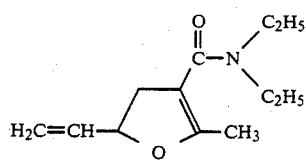

Boiling Point 90°–95° C. at 0.01 mm Hg.
nmr(CDCl$_3$) δ 1.17(t, 6H(—N(CH$_2$CH$_3$)$_2$)); 1.88(t,3H methyl); 2.40–3.35(m, 2H(2 methylene ring H, partially hidden)); 3.42(q, 4H(—N(CH$_2$CH$_3$)$_2$)); 4.90–5.52(m, 3 vinyl H); 5.75–6.37(m, 1 ring H).

EXAMPLE II

Utilizing a phase-transfer procedure similar to that described in Example I, phenylsulfonylacetone was reacted with 1,4-dichlorobutene-2 to obtain 1-phenylsulfonyl-1-acetyl-2-vinylcyclopropane. For the reaction, 9.91 grams phenylsulfonylacetone (Parish Chemical Co.) and 6.25 grams 1,4-dichlorobutene-2 were combined in 20 mls sulfolane containing 6.6 grams potassium hydroxide (85%) and 5 mole percent tricaprylylmethylammonium chloride. The reaction mixture was stirred at 35°–40° C. for 3½ hours. One-hundred mls water was then added to dissolve the white granular precipitate which had formed and the mixture extracted several times with ether. A crude red oil (10.8 grams) was obtained after removal of the ether and further work-up utilizing a Waters Preparatory Liquid Chromatograph 500A equipped with a gel permeation column and operated at a flow rate of 0.1 l/min yielded the cis and trans isomers of 1-phenylsulfonyl-1-acetyl-2-vinylcyclopropane.

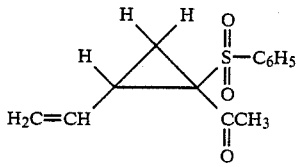

trans 1-phenylsulfonyl-1-acetyl-2-vinylcyclopropane
nmr(CDCl$_3$) τ 1.80–2.37(5 phenyl H, mult.); 4.20–4.75(3 vinyl H, mult.); 6.60–7.75(1H(2 cyclopropyl ring position), b mult.); 7.60(3H(CH$_3$CO—),s.); 7.85–8.2(2H(3 cyclopropyl ring position), mult.).
cis 1-phenylsulfonyl-1-acetyl-2-vinylcyclopropane
nmr(CDCl$_3$) τ 1.80–2.45(5 phenyl H, mult.); 3.45–5.05(3 vinyl H, br. vinyl pattern); 7.60(1H(2 cyclopropyl ring position), br. mult. centered at 7.50τ); 7.55(3H(CH$_3$CO—), s.); 8.00–9.15(2H(3 cyclopropyl ring position), well defined mult.).

A portion of the product, consisting of a mixture of the cis and trans isomers, was combined with 15 mole percent tricaprylylmethylammonium chloride and heated at 110° C. for 1½ hours to effect isomerization of the 1-phenylsulfonyl-1-acetyl-2-vinylcyclopropane to 4-phenylsulfonyl-5-methyl-2-vinyl-2,3-dihydrofuran.

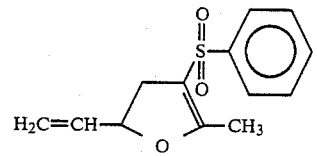

nmr(CDCl$_3$) δ 2.27(t, 3H methyl); 2.49–3.48(m,2H(2 methylene ring H)); 4.82–5.53(m, 3 vinyl H); 5.70–6.30(m, 1 ring H); 7.45–8.19(m, 5 phenyl H).

EXAMPLE III 1,4-Dichlorobutene-2 (50 grams) and potassium hydroxide (26.2 grams) were combined in 400 mls methylene chloride containing 8.06 grams tricaprylylmethylammonium chloride. Acetoacetanilide (35.4 grams) was then slowly added, and after the addition was complete, the reaction was continued for 4 hours at room temperature. Essentially pure 1-acetyl-2-vinylcyclopropanecarboxanilide

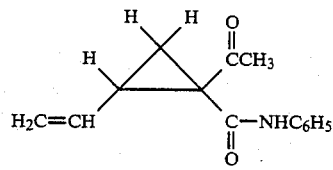

was obtained upon work-up of the reaction mixture and recrystallization from isopropanol.
Melting point 104°–104.7° C.
Mass spectrum m/e 229(M+)
nmr(CDCl$_3$) τ 0.10(1H(—CONH—), br. s.); 2.25–2.95(5 phenyl H, mult.); 4.15–4.9(3 vinyl H, mult.); 7.10–7.60(1H(2 ring position), mult.); 7.76(3H(—COCH$_3$), s.); 7.10–8.30(2H(3 ring position), mult. (partially hidden)).

1-Acetyl-2-vinylcyclopropanecarboxanilide (2 grams) was combined with 0.5 grams tributylhexadecylammonium bromide and heated for six hours to obtain essentially complete conversion to 4-phenylcarbamyl-5-methyl-2-vinyl-2,3-dihydrofuran.

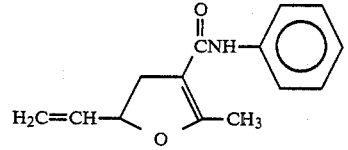

nmr(CDCl$_3$) δ 2.20(t, 3H methyl); 2.35–3.35(m, 2H(2 methylene ring H); 4.70–5.50(m, 3 vinyl H); 5.67–6.30(m, 1 ring H); 7.00–7.80(m, 5 phenyl H).
IR(KBr) 3290, 1660, 1620, 1598, 1520, 1502, 1491, 1445, 1380, 1338, 1262, 1149, 971, 759 and 691 cm$^{-1}$

EXAMPLE IV

To demonstrate the utility of the 2,3-dihydrofuran derivatives of the present invention and their use as fungicides, 4-phenylcarbamyl-5-methyl-2-vinyl-2,3-dihydrofuran and 4-phenylcarbamyl-5-methyl-2-ethyl- 2,3-dihydrofuran were evaluated to determine their fungistatic activity against three known plant pathogens: *Helminthosporium gramineum* ATTC No. 11254, from the class *fungi imperfecti* which is isolated from barley grain; *Fusarium nivale* ATCC No. 18221, a parasite of oats; and *Fusarium culmorum* ATCC No. 36017, a parasite of corn. Each compound was evaluated at 10, 100 and 1000 ppm. These dilutions were prepared from a 10,000 ppm stock solution made in 1:1 acetone in water. Eleven (11) mls of each test concentration was added to 99 mls melted Potato Dextrose Agar and three Petrie dishes poured for each concentration of each material being evaluated. After the plates hardened, they were streaked with the selected test organism. Three control plates containing the medium but no test material, were also streaked with the test organism. Results were as follows:

| SAMPLE | TEST CONC. (PPM) | GROWTH ZONE SITE (IN MM) ON REPLICATE PLATES | | | MEAN ZONE SIZE |
| --- | --- | --- | --- | --- | --- |
| | | 1 | 2 | 3 | |
| *HELMINTHOSPORIUM GRAMINEUM* INCUBATED 5 DAYS @ 25° C.: | | | | | |
| 4-phenylcarbamyl-5-methyl-2-vinyl-2,3-dihydrofuran | 10 | 35 | 37 | 35 | 35.7 |
| | 100 | 24 | 24 | 21 | 23.0 |
| | 1000 | 0 | 0 | 0 | 0.0 |
| 4-phenylcarbamyl-5-methyl 2-ethyl-2,3-dihydrofuran | 10 | 37 | 38 | 36 | 37.0 |
| | 100 | 20 | 23 | 23 | 22.0 |
| | 1000 | 0 | 0 | 0 | 0.0 |
| Control | — | 35 | 34 | 37 | 35.3 |
| *FUSARIUM CULMORUM* INCUBATED 5 DAYS @ 25° C.: | | | | | |
| 4-phenylcarbamyl-5-methyl 2-vinyl-2,3-dihydrofuran | 10 | 73 | 74 | 74 | 74.3 |
| | 100 | 56 | 55 | 55 | 55.4 |
| | 1000 | 17 | 23 | 25 | 21.7 |
| 4-phenylcarbamyl-5-methyl-2-ethyl-2,3-dihydrofuran | 10 | 70 | 70 | 70 | 70.0 |
| | 100 | 20 | 20 | 22 | 20.7 |
| | 1000 | 7 | 8 | 7 | 7.3 |
| Control | — | 77 | 80 | 78 | 78.3 |
| *FUSARIUM NIVALE* INCUBATED 12 DAYS @ 25° C.: | | | | | |
| 4-phenylcarbamyl-5-methyl-2-vinyl-2,3-dihydrofuran | 10 | 25 | 35* | 35* | 31.7 |
| | 100 | 17 | 0 | 0 | 5.7 |
| | 1000 | 0 | 0 | 0 | 0.0 |
| 4-phenylcarbamyl-5-methyl-2-ethyl-2,3-dihydrofuran | 10 | 0 | 45 | 50 | 31.7 |
| | 100 | 43 | 30 | 45* | 39.3 |
| | 1000 | 0 | 0 | 0 | 0.0 |
| Control | — | 65* | 60* | 74* | 66.3 |

[*Indicates measurement of growth of single colony, line of growth failed to appear.]

The fungistatic activity of the products of this invention is evident by a comparison of the amount of growth obtained on the plates containing the 2,3-dihydrofuran compounds with the amount of growth obtained on the control plates.

We claim:

1. 4-Diethylcarbamyl-5-methyl-2-vinyl-2,3-dihydrofuran.

2. 4-Phenylcarbamyl-5-methyl-2-vinyl-2,3-dihydrofuran.

3. 4-Phenylsulfonyl-5-methyl-2-vinyl-2,3-dihydrofuran.

4. A method of inhibiting the growth of fungi which comprises contacting said fungi with a fungicidally effective amount of a compound of the formula

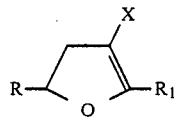

wherein R is an ethyl or vinyl group, $R_1$ is a $C_{1-4}$ alkyl group and X is selected from the group consisting of nitrile;

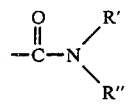

and R' is $C_{1-4}$ alkyl or phenyl and R'' is hydrogen, $C_{1-4}$ alkyl or phenyl; and

where R''' is $C_{1-10}$ alkyl, phenyl, benzyl, $C_{1-4}$ alkyl- or alkoxyl-substituted phenyl or benzyl or the group $$-N\begin{matrix} R' \\ R'' \end{matrix}$$

where R' is $C_{1-4}$ alkyl or phenyl and R'' is hydrogen, $C_{1-4}$ alkyl or phenyl.

* * * * *

UNITED STATES PATENT AND TRADEMARK OFFICE
CERTIFICATE OF CORRECTION

PATENT NO. : 4,522,950
DATED      : June 11, 1985
INVENTOR(S): Allen L. Hall and Richard G. Fayter, Jr.

It is certified that error appears in the above-identified patent and that said Letters Patent are hereby corrected as shown below:

Column 6, line 61, --- 1534 --- should be inserted after "1598"; line 62, --- 1228 --- should be inserted after "1262".

Column 7, in the Table under the column headed "1", --- * --- should be inserted after "17", second instance.

Signed and Sealed this

Twenty-ninth Day of October 1985

[SEAL]

Attest:

Attesting Officer

DONALD J. QUIGG

Commissioner of Patents and Trademarks—Designate